United States Patent [19]

Marshall et al.

[11] Patent Number: 4,486,432
[45] Date of Patent: Dec. 4, 1984

[54] QUINOXALINEDIONE LEUKOTRIENE RELEASE INHIBITORS

[75] Inventors: Winston S. Marshall, Bargersville; Jerome H. Fleisch, Indianapolis; George J. Cullinan, Trafalger, all of Ind.

[73] Assignee: Eli Lilly and Company, Indianapolis, Ind.

[21] Appl. No.: 430,896

[22] Filed: Sep. 30, 1982

[51] Int. Cl.$^3$ .................. C07D 241/42; A61K 31/495
[52] U.S. Cl. ..................................... 424/250; 544/353
[58] Field of Search ........................ 544/353; 424/250

[56] References Cited

U.S. PATENT DOCUMENTS 3,890,319  6/1975  Danielewcz et al. ............... 544/353

OTHER PUBLICATIONS

Ford, K. H.; Joullié, M. M., J. of Hef. Chem. 3, 529, (1966).

*Primary Examiner*—Mark L. Berch
*Attorney, Agent, or Firm*—Leroy Whitaker; Arthur R. Whale

[57] ABSTRACT

This invention provides for novel quinoxalinedione derivatives, the use of quinoxalinedione derivatives in treating animals suffering from immediate hypersensitivity reactions and conditions characterized by excessive release of leukotrienes, and formulations of the quinoxalinedione derivatives.

12 Claims, No Drawings

QUINOXALINEDIONE LEUKOTRIENE RELEASE INHIBITORS

BACKGROUND OF THE INVENTION

Slow reacting substances of anaphylaxis (SRS-A), or leukotrienes, are naturally occurring substances which cause the constriction of smooth muscle, especially bronchial muscle. The excessive release of these substances has been found to be associated with a variety of allergic and inflammatory conditions, including immediate type hypersensitivity reactions such as asthma. Additionally, evidence obtained over the past few years has shown the presence of leukotrienes in sputum of patients wich chronic bronchitis (Turnbull, et al., *Lancet* II, 526 (1977)) and cystic fibrosis (Cromwell, et al., *Lancet* II, 164 (1981)) suggesting a role of leukotrienes in the pathology of those diseases.

Thus, compounds which inhibit the release of leukotrienes are indicated for a variety of conditions, including asthma, in which leukotrienes are a factor.

A series of 6-anilino-5,8-quinoxalinediones was prepared by Ford and Joullié, *J. Het. Chem.*, 3, 529 (1966), including p-fluoro-, p-chloro-, p-bromo-, and p-methylanilino-2,3-dimethyl-5,8-quinoxalinedione; no biological activity was reported for these compounds.

This invention relates to a class of quinoxalinediones, which are useful as inhibitors of leukotriene release and for the therapy of immediate hypersensitivity reactions and conditions characterized by excessive release of leukotrienes.

SUMMARY OF THE INVENTION

According to the present invention there is provided a compound of formula (I)

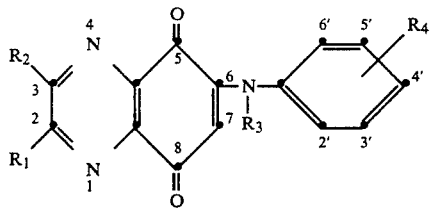

wherein $R_1$, $R_2$ and $R_3$, are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl;

With the provision that when one of $R_1$ and $R_2$ is methyl and the other of $R_1$ and $R_2$ is methyl or ethyl, and $R_3$ is hydrogen, $R_4$ is not halo or $C_1$–$C_2$ alkyl.

In addition to the compounds of formula I, this invention also provides a method of treating a mammal suffering from or susceptible to an immediate hypersensitivity reactions of the type represented by asthma or any condition characterized by an excessive release of leukotrienes, which comprises administering to said mammal a therapeutically effective amount of a compound of formula (II)

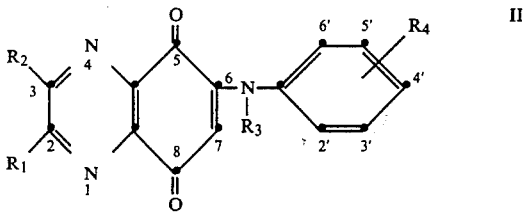

wherein $R_1$, $R_2$, and $R_3$ are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl.

According to a further aspect of the present invention there is provided a pharmaceutical formulation which comprises as active ingredient a therapeutically effective amount of a compound of formula (II) as defined above, associated with a pharmaceutically acceptable carrier therefor.

DETAILED DESCRIPTION AND PREFERRED EMBODIMENT

The following definitions refer to the various terms used throughout this disclosure.

The term "halo" refers to fluoro, chloro, bromo, and iodo.

The term "$C_1$–$C_6$ alkyl" refers to the straight and branched aliphatic radicals of one to six carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl and the like. The term "$C_1$–$C_6$ alkyl" includes the term "$C_1$–$C_2$ alkyl" and "$C_1$–$C_3$ alkyl".

The term "$C_1$–$C_6$ alkoxy" includes the straight and branched aliphatic ether radicals of one to six carbon atoms such as methoxy, ethoxy, propoxy, isopropoxy, butoxy, isobutoxy, sec-butoxy, tert-butoxy, and the like.

Preferred compounds of this invention are those wherein:

(a) $R_1$ is hydrogen,
(b) $R_2$ is hydrogen,
(c) $R_3$ is hydrogen, and
(d) $R_4$ is halo, especially fluoro.

Especially preferred compounds are those wherein:

(a) each of $R_1$, $R_2$, and $R_3$ is hydrogen, and
(b) $R_4$ is fluoro, especially in the meta- or 3'-position, with 6-(3-fluoroanilino)-5,8-quinoxalinedione being the most preferred compound.

The preparation of the 5,8-quinoxalinedione compounds of this invention is performed by the following reaction scheme:

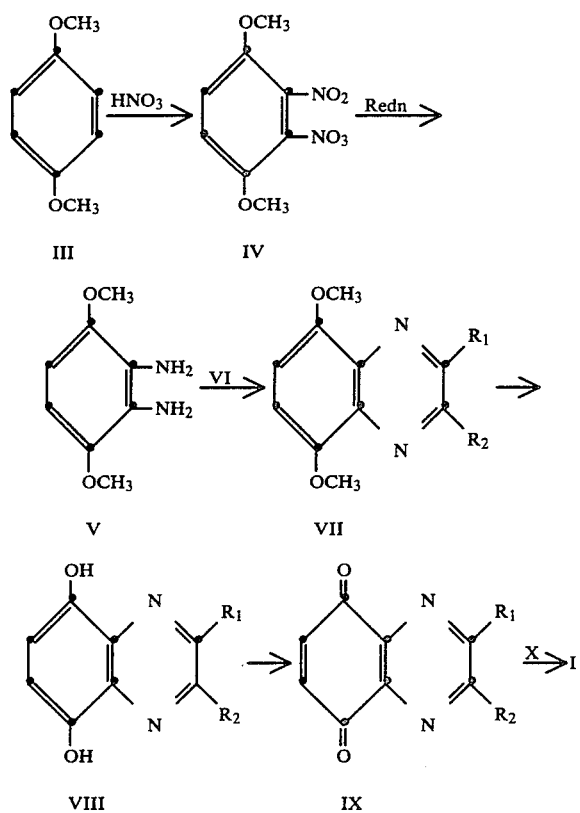

The transformation of p-dimethoxybenzene (III) to the corresponding diamine (V) is described by King, et al., *J. Chem. Soc.*, 3012 (1949). Thus, a solution of p-dimethoxybenzene in acetic or sulfuric acid is treated with nitric acid at a temperature of 0°–100° C. After heating at 50°–100° C. for 5–15 minutes, and isolation by filtration after addition of the reaction solution to water, the resulting mixture of 2,3- and 2,5-dinitro-1,4-dimethoxybenzenes is converted to the corresponding mixture of diamines. This reduction may be performed chemically, for instance, by aqueous treatment with sodium hydrosulfite or treatment with zinc, tin, or iron in the presence of a mineral acid such as hydrochloric acid, or preferably by catalytic hydrogenation. Catalytic hydrogenation may be performed in a non-reactive solvent, such as alcohols or ethers, employing a suitable catalyst such as Raney nickel, platinum oxide, palladium-on-carbon, and the like.

The diamines thus formed may be separated by crystallization or by chromatographic separation, or used together in the sub subsequent reaction with a dione of the formula

  VI where $R_1$ and $R_2$ are the same as previously defined.

This transformation has been described by King (supra) and Adachi (*Chemical Abstracts*, 51, 17936b) using an adduct of glyoxal (VI, $R_1$ and $R_2$ are each hydrogen) with sodium bisulfite. The reactions with other diones of formula VI are performed in a similar manner, by reacting the diamine V with VI in a protic solvent, such as water or alcohols, at a temperature of 20°–100° C. usually in the presence of a small amount of an acid, such as a mineral acid. Upon the addition of a base, such as sodium hydroxide, and the removal of the organic solvent, if any, the desired product VII precipitates upon cooling. In the case above where a mixture of the diamines is used in the reaction with VI, the unreacted 2,5-diamine precipitates first upon addition of the base to the reaction solution and may be removed by filtration. Other by-products usually stay in solution while VII then precipitates out of solution. Alternatively, chromatography and/or crystallization may be used to purify the desired product VII.

The demethylation of VII to the dihydroxy derivative VIII is also described by Adachi (supra) by refluxing the dimethoxy compound VII with aluminum chloride in a non-reactive solvent such as benzene. The demethylation may also be performed by heating in hydrobromic acid/acetic acid in the usual manner.

The oxidation of 5,8-dihydroxyquinoxaline (VIII) to the corresponding dione (IX) was reported by Adachi (supra) by treating with silver (I) oxide.

Alternatively, the dimethoxy compound (VII) may be converted to the dione (IX) directly by the action of the silver catalyst described in *Chemistry Letters*, 1980, 725, upon VII in the presence of aqueous acetonitrile, or by the action of silver (II) oxide in the presence of nitric acid as described by Farina and Torres, *Synthesis*, Sept. 1980, 753.

Treatment of the 5,8-quinoxalinedione (IX) with anilines of the formula

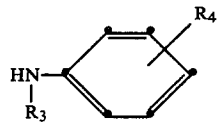  X where $R_3$ and $R_4$ are the same as described above produces the desired compounds of this invention. The general procedure used is similar to that described by Ford and Joullié, *J. Het. Chem.*, 3, 529 (1966). A solution of the aniline X, usually a 2–5 molar excess, is added to a solution of the dione IX in the presence of a solvent such as an ether, for example 1,2-dimethoxyethane, or an alcohol, for example ethanol. The reaction is usually allowed to proceed at room temperature, although elevated temperatures, up to the reflux temperature of the solvent, may be employed. Additionally, the introduction of catalytic amounts of cerium chloride is desirable in order to facilitate the condensation. See Pratt, *J. Org. Chem.*, 27, 3905 (1962). The reaction is worked up in the usual manner and the desired product may be purified by conventional means, such as crystallization or chromatography.

It is also possible to combine certain steps of the synthesis. For instance, 5,8-dihydroxyquinoxaline (VIII, $R_1$ and $R_2$ are hydrogen) may be converted directly to 6-(3-fluoroanilino)-5,8-quinoxalinedione (I, $R_1$, $R_2$, and $R_3$ are hydrogen, $R_4$ is 3′-fluoro) by heating with 3-fluoroaniline and silver (I) oxide.

It is recognized that in the situation where $R_1$ and $R_2$ are different, two different isomers may be formed when the aniline X is condensed with the dione IX or the diol VIII. Separation of the two isomers may be achieved by crystallization or chromatography in the normal manner.

The preparation of the quinoxalinedione compounds of this invention are described in the following examples. The examples are illustrative of the compounds embraced by the invention and of the methods commonly employed in their preparation, but are not to be construed as limiting the invention. The term "m/e" used in characterizing the products refers to the mass-to-charge ratio of ions which appear in the mass spectra of the products. In general, the values correspond to molecular weights of the major peaks, and are so designated "M+".

EXAMPLE 1

Preparation of 5,8-dihydroxyquinoxaline

Ten grams of 5,8-dimethoxyquinoxaline were dissolved in 100 ml. of glacial acetic acid. After 60 ml. of 48% hydrobromic acid were added to the solution, the reaction was allowed to reflux overnight. The solution was evaporated to dryness in vacuo and a solution of 5% sodium bicarbonate was added until the reaction was basic. The solution was extracted several times with methylene chloride. The combined methylene chloride extracts were dried with sodium sulfate and evaporated to give an amorphous powder which was used without purification for the subsequent reactions.

EXAMPLE 2

Preparation of 5,8-quinoxalinedione (A) The title compound was perpared from 5,8-dihydroxyquinoxaline according to the procedure of Adachi (Chemical Abstracts, 51, 17936b).

(B) The title compound was also prepared in the following manner

A silver (II) catalyst was prepared according to *Chemistry Letters,* 1980, 725. Pyridine-2,6-dicarboxylic acid (33.4 g.) was suspended in 4 liters of water and 16.9 g. of silver nitrate were added. Over a one hour period, 135 g. of potassium peroxydisulfate were added. After stirring at room temperature overnight, the catalyst was collected by filtration, washed with water, and dried, giving 43 g. of black needles.

A suspension of 22 g. of the silver catalyst prepared above, 148 ml. of acetonitrile, and 32 ml. of water was added over a 30 minute period to 2.0 g. of 5,8-dimethoxyquinoxaline. The reaction was stirred for two hours at room temperature. The catalyst was filtered off and washed with methylene chloride. Water was added to the filtrate and the filtrate was then extracted with the methylene chloride used to wash the catalyst. The methylene chloride was dried over sodium sulfate and evaporated to give the title compound as a brown powder which was used without further purification.

(C) The title compound was also prepared in the following manner, following the procedure of Farina and Torres, *Synthesis,* Sept. 1980, 753.

To a solution of 7.6 g. of 5,8-dimethoxyquinoxaline in 400 ml. of dioxane were added 20 g. of silver (II) oxide. After stirring for about five minutes, 40 ml. of 6N nitric acid were added. After stirring overnight at room temperature, the reaction was filtered. The filter residue was boiled in about 400 ml. of water and filtered hot. About 100 ml. of saturated brine were added to the filtrate and the resulting yellow-white precipitate was removed by filtration. The resulting dark brown solution containing the title compound was used as is for the subsequent transformations.

EXAMPLE 3

Preparation of 6-anilino-5,8-quinoxalinedione

Approximately 2 g. of 5,8-quinoxalinedione were dissolved in 200 ml. of 2B ethanol. Aniline (1.2 g.) was added and the reaction was stirred overnight at room temperature. The reaction was evaporated, water was added, and the mixture was extracted several times with methylene chloride. The combined extracts were dried over sodium sulfate and evaporated to dryness. The residue was chromatographed over a silica gel column, eluting with ethyl acetate. The desired fractions were combined and evaporated. The material was crystallized from ethyl acetate to give 50 mg. of the title product as a red powder, m.p. about 203°–205° C.

Analysis: $C_{14}H_9N_3O_2$; Calc.: C, 66.93; H, 3.61; N, 16.73; Found: C, 69.02; H, 4.11; N, 17.00.

EXAMPLE 4

Preparation of 6-(N-methylanilino)-5,8-quinoxalinedione

When the procedure of Example 3 was repeated using 2 g. of N-methylaniline instead of aniline, 700 mg. of the title product were obtained as crystals from ethyl acetate/hexane, m.p. about 207°–208° C.

Analysis: $C_{15}H_{11}N_3O_2$; Calc.: C, 67.92; H, 4.18; N, 15.84; Found: C, 67.82; H, 4.33; N, 15.53.

EXAMPLE 5

Preparation of 6-(2-fluoroanilino)-5,8-quinoxalinedione

Approximately 350 ml. of an aqueous solution of 5,8-quinoxalinedione (see Example 2C), 3 g. of 2-fluoroaniline, and 5 g. of cerium chloride were stirred together at room temperature overnight. The reaction was extracted with methylene chloride. The methylene chloride extract was washed with water, dried over sodium sulfate, and evaporated to dryness. The residue was chromatographed over silica gel eluting with ethyl acetate. The desired fractions were combined and the solvent evaporated. The residue was crystallized from ethyl acetate affording about 100 mg. of the title compound as red plates. Mass spectrum gave M+ of 269.

Analysis: $C_{14}H_8FN_3O_2$; Calc.: C, 62.46; H, 3.00; N, 15.61; F, 7.06; Found: C, 57.78; H, 3.07; N, 14.41; F, 5.83.

EXAMPLE 6

Preparation of 6-(3-chloroanilino)-5,8-quinoxalinedione

Following the procedure of Example 5,3-chloroaniline was reacted with the aqueous solution of 5,8-dimethoxyquinoxaline in the presence of cerium chloride to give the title compound. Mass spectrum gave M+ of 285 and 287.

Analysis: $C_{14}H_8ClN_3O_2$; Calc.: C, 58.86; H, 2.82; N, 14.71; Found: C, 60.78; H, 2.94; N, 15.35.

EXAMPLE 7

Preparation of 6-(3-fluoroanilino)-5,8-quinoxalinedione

Approximately one gram of 5,8-dihydroxyquinoxaline was dissolved in 100 ml. of 2B ethanol. To the solution were added about 5 g. of freshly prepared silver (I) oxide and about 3 g. of 3-fluoroaniline. The reaction was stirred overnight at room temperature and worked up in the same manner as described in Example 3. Crystallization from ethyl acetate gave about 500 mg. of the title compound.

Analysis: $C_{14}H_8FN_3O_2$; Calc.: C, 62.46; H, 3.00; N, 15.61; F, 7.06; Found: C, 62.69; H, 3.26; N, 15.35; F, 6.94.

EXAMPLE 8

Preparation of 6-anilino-2,3-dimethyl-5,8-quinoxalinedione

Following the procedure of Example 7,2,3-dimethyl-5,8-dihydroxyquinoxaline and aniline were reacted to give the title product which was purified by chromatography over silica gel, eluting with ethyl acetate, and crystallization from ethyl acetate/hexane.

Analysis: $C_{16}H_{13}N_3O_2$; Calc.: C, 68.81; H, 4.69; N, 15.05; Found: C, 69.51; H, 4.96; N, 14.11.

The compounds of Formula II are useful in inhibiting the release of SRS-A as demonstrated by the following test procedure Male, Hartley guinea pigs, usually 1–2 weeks old were sensitized with respect to ovalbumin by intraperitoneal administration of 0.15 ml. hyperimmune serum obtained from guinea pigs actively sensitized against ovalbumin. After 2 days or more, the animals were decapitated, lungs were excised and perfused through the pulmonary artery with Krebs' bicarbonate solution of the following composition in mmoles/liter: KCl, 4.6; $CaCl_2.2H_2O$, 1.8; $KH_2PO_4$, 1.2; $MgSO_4.7H_2O$, 1.2; NaCl, 118.2; $NaHCO_3$, 24.8; and dextrose, 10.0. Poorly perfused and bloody areas were discarded. Normal lung was cut into 1 mm. cubes with a McIlwain tissue chopper, washed with Krebs' solution and divided into 400 mg. aliquots. The fragmented tissue was then incubated at 37° C. for 15 minutes in Krebs' solution containing indomethacin to optimize SRS-A release and an appropriate concentration of experimental drug. Antigen (ovalbumin) was then added to make a final concentration of $1 \times 10^{-5}$ g./ml. Fifteen minutes later, the incubation medium was decanted and centrifuged at $3,000 \times g$ at 4° C. for 5 minutes. The supernatant solution was collected and assayed for SRS-A using a computerized bioassay that employs the isolated guinea pig ileum (Fleisch et al., *J. Pharmacol. Exp. Ther.*, 209, 238–243, (1979)). Release of SRS-A in the presence of an experimental drug was compared to a control sample and the results expressed as percent inhibition of SRS-A release. These results are shown in Table I:

TABLE I

| | Inhibition of SRS-A Release | | | | |
|---|---|---|---|---|---|
| | Percent Inhibition Drug Concentration | | | | |
| Compound of Example No. | $3 \times 10^{-5}M$ | $1 \times 10^{-5}M$ | $3 \times 10^{-6}M$ | $1 \times 10^{-6}M$ | $3 \times 10^{-7}M$ |
| 3 | 75 | NT* | 22 | 8 | ND** |
| 4 | 59 | 18 | NT | 22 | NT |
| 5 | 83 | NT | 12 | NT | NT |
| 6 | 71 | NT | 28 | NT | NT |
| 7 | 81 | 67 | 48 | 22 | 6 |
| 8 | NT | NT | 40 | 31 | NT |

*Not tested
**Not tested - 0% at $1 \times 10^{-7}M$

The compounds or formulations of the present invention may be administered by the oral and rectal routes, topically, parenterally, e.g. by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg, in the case of parenteral administration, from 5.0 to 50 mg. in the case of inhalation and from 25 to 500 mg. in the case of oral or rectal administration) of a compound of Formula II. Dosages of from 0.5 to 300 mg./kg. per day, preferably 0.5 to 20 mg./kg. of active ingredient may be administered although it will, of course, readily be understood that the amount of the compound or compounds of Formula II actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of formula II mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred is a formulation for inhalation application, such as an aerosol.

We claim:

1. A compound of Formula I

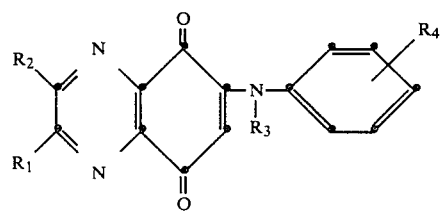

wherein $R_1$, $R_2$ and $R_3$, are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl, with the provision that when one of $R_1$ and $R_2$ is methyl and the other of $R_1$ and $R_2$ is methyl or ethyl, and $R_3$ is hydrogen, $R_4$ is not halo or $C_1$–$C_2$ alkyl.

2. A compound of claim 1 wherein $R_1$, $R_2$, and $R_3$ are all hydrogen.

3. The compound of claim 2 which is 6-(3-fluoroanilino)-5,8-quinoxalinedione.

4. A method of treating a mammal suffering from or susceptible to any condition characterized by an excessive release of leukotrienes, which comprises administering to said mammal a therapeutically effective amount of a compound of formula II

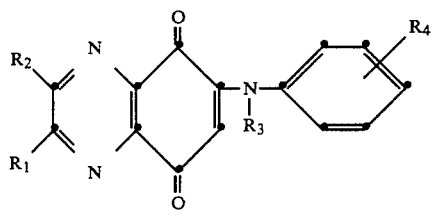

wherein $R_1$, $R_2$, and $R_3$ are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl.

5. The method of claim 4 wherein $R_1$, $R_2$, and $R_3$ of Formula II are each hydrogen.

6. The method of claim 5 wherein the compound is 6-(3-fluoroanilino)-5,8-quinoxalinedione.

7. A method of treating a mammal suffering from or susceptible to an immediate hypersensitivity reaction of the type represented by asthma, which comprises administering to said mammal a therapeutically effective amount of a compound of formula II

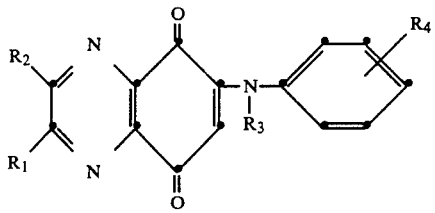

wherein $R_1$, $R_2$, and $R_3$ are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl.

8. The method of claim 7 wherein $R_1$, $R_2$, and $R_3$ of Formula II are each hydrogen.

9. The method of claim 7 wherein the compound is 6-(3-fluoroanilino)-5,8-quinoxalinedione.

10. A pharmaceutical formulation comprising a compound of formula II

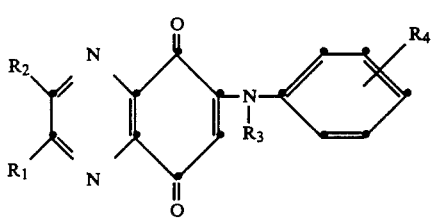

wherein $R_1$, $R_2$, and $R_3$ are each independently hydrogen or $C_1$–$C_6$ alkyl; and $R_4$ is $C_1$–$C_6$ alkyl, $C_1$–$C_6$ alkoxy, halo, trifluoromethyl, nitro, hydroxy, $C_1$–$C_3$ alkylthio, or $C_1$–$C_3$ alkylcarbonyl, in association with a pharmaceutically acceptable carrier.

11. The pharmaceutical formulation of claim 10 wherein the compound is 6-(3-fluoroanilino)-5,8-quinoxalinedione.

12. The pharmaceutical formulation of claim 11 which is formulated for inhalation.

* * * * *